United States Patent [19]

DeLuca et al.

[11] Patent Number: 5,397,776

[45] Date of Patent: Mar. 14, 1995

[54] VITAMIN D COMPOUNDS WITH ANTI-PROGESTERONE ACTIVITY

[75] Inventors: Hector F. DeLuca, Deerfield; Kato L. Perlman; Hisham M. Darwish, both of Madison, all of Wis.

[73] Assignee: Wisconsin Alumni Research Foundation, Madison, Wis.

[21] Appl. No.: 110,120

[22] Filed: Aug. 20, 1993

[51] Int. Cl.⁶ .............................................. A61K 31/59
[52] U.S. Cl. .................................................. 514/167
[58] Field of Search ............... 514/691, 693, 729, 703, 514/167

[56] References Cited

FOREIGN PATENT DOCUMENTS 0184112  6/1986  European Pat. Off. .

OTHER PUBLICATIONS

Kumar et al. Vitamin D and Calcium Hormones in Pregnancy. *N. Eng. J. Med.* 1980; 302(20); 1143–4.
"Synthesis and Biological Activity of 3β-Hydroxy-9,-10-Secopregna-5,7,10[19]-Triene-20-One: A Side Chain Analogue of Vitamin D₃", Murari et al, Biochem, vol. 17, 1982, pp. 615–619.

*Primary Examiner*—Raymond G. Henley, III
*Assistant Examiner*—Phyllis G. Spivack
*Attorney, Agent, or Firm*—Andrus, Sceales, Starke & Sawall

[57] ABSTRACT

A birth control method for a female mammal which comprises administering to the mammal an amount of a vitamin D compound sufficient to block binding of progesterone to the progesterone receptor in said mammal.

15 Claims, No Drawings

VITAMIN D COMPOUNDS WITH ANTI-PROGESTERONE ACTIVITY

This invention relates to biologically active vitamin D analogues useful as antagonists of progesterone suggesting a potential use for birth control.

BACKGROUND AND SUMMARY OF THE INVENTION

The 1α-hydroxylated metabolites of vitamin D—most importantly 1α,25-dihydroxyvitamin $D_3$ and 1α,25-dihydroxyvitamin $D_2$—are known as highly potent regulators of calcium homeostasis in animals and humans, and more recently their activity in cellular differentiation has also been established. V. Ostrem et al, Proc. Natl. Acad. Sci. USA, (1987), 84, 2610. As a consequence, many structural analogues of these metabolites, such as compounds with different side chain structures, different hydroxylation patterns, or different stereochemistry, have been prepared and tested. Important examples of such analogues are 1α-hydroxyvitamin $D_3$, 1α-hydroxyvitamin $D_2$, various side chain fluorinated derivatives of 1α,25-dihydroxyvitamin $D_3$, and side chain homologated analogues. Several of these known compounds exhibit highly potent activity in vivo or in vitro, and some of these have been found to exhibit an interesting separation of activities in cell differentiation and calcium regulation. This difference in activity provides these compounds with advantageous therapeutic activity profiles and thus numerous of these compounds are in use, or have been proposed for use, in the treatment of a variety of diseases such as renal osteodystrophy, vitamin D-resistant rickets, osteoporosis, psoriasis, and certain malignancies.

Recently, a new class of vitamin D analogues has been discovered, i.e. the so-called 19-nor-vitamin D compounds. 19-nor-vitamin D compounds are vitamin D analogues in which the ring A exocyclic methylene group (carbon 19) typical of all vitamin D compounds has been removed and replaced by two hydrogen atoms. Specifically, these compounds exhibit a selective activity profile with high potency in inducing cellular differentiation, and minimal bone calcification activity. Such a differential activity profile renders these compounds useful for the treatment of malignancies, or the treatment of various skin disorders. Two different methods of synthesis of these 19-nor-vitamin D analogues have been described (Perlman et al, Tetrahedron Letters 31, 1823 (1990); Perlman et al, Tetrahedron Letters 32, 7663 (1991), and DeLuca et al, U.S. Pat. No. 5,086,191).

In Teutsch et al, U.S. Pat. No. 4,386,085, a 19-norsteroid (referred to as RU 486) having strong antiprogesterone and antiglucocorticosteriod activities is described. When used in conjunction with synthetic prostaglandins RU 486 terminates pregnancy, which accounts for its wide interest. In addition it has potential as an antiglucocorticoid, and antiestrogen agent.

Many analogues of RU 486 have been prepared, Etienne-Emile Baulieu: Science (1989) 245, 1351–1357, Chem. Eng. News (1991) 69 7–14, Schering's ZK 98299 (Federation Meeting 1992) 2037, all of which share with RU 486 the intact steroid A ring of progesterone with the conjugated 3-oxo-4-ene moiety. This feature is assumed to be responsible for binding to the progesterone receptor (PR).

In an ongoing effort to examine the many different aspects of the vitamin D molecule vitamin D analogues with the CD ring of progesterone, but with the 3β-hydroxycyclohexane A-ring and double bond system characteristic of vitamin D have now been synthesized. The compounds prepared were 20-oxo-pregnacalciferol, 1α-hydroxy-20-oxopregnacalciferol and 19-nor-1α-hydroxy-20-oxopregnacalciferol and their binding to the PR examined. One of these, 20-oxo-pregnacalciferol was synthesized earlier in calcemic studies using a classical multi step procedure from pregnenolone acetate, M. P. Murari et al, J. Steroid Biochem. (1982) 17, 615–619. The product was obtained in extremely poor yield, and was shown to have no significant calcemic activity.

All three compounds were examined for binding to the PR. Of the three 20-oxo analogues, only 20-oxo-pregnacalciferol (compound 3 in the accompanying Scheme) did bind to the PR, indicating that the 1α-hydroxy group in the other two vitamin D-progesterone analogues (compounds 6 and 9 in the accompanying Scheme) prevents binding to the PR, and the absence of the 10-19 double bond in compound 9 did not make a difference. None of the above three compounds had any calcemic activity nor did they bind to the vitamin D receptor.

It has been suggested, Teutsch et al, U.S. Pat. No. 4,386,085 May 31, 1983, Etienne-Emile Baulieu: Science (1989) 245, 1351–1357, that the A ring of RU 486 is necessary for binding to the PR. The ability of compound 3 to bind to the PR despite the absence of the A ring suggests that the progesterone A ring may not play as significant a role as had been assumed. 20-oxopregnacalciferol is the first vitamin D type compound which binds to the PR with potential of interesting new activities in this field. In particular, it appears that 20-oxopregnacalciferol is useful as an antagonist of progesterone, and thus blocks progesterone from binding to the PR. Since progesterone binding is necessary to maintain pregnancy, an abortion results. This compound, and similar vitamin D compounds, thus have potential for use in birth control either to prevent pregnancy or to abort pregnancy. For example, it has been discovered that the vitamin D 22-aldehyde (compound 12 in the accompanying Scheme) and the vitamin D 22-alcohol (compound 13 in the accompanying Scheme) also bind to the PR.

DISCLOSURE OF THE INVENTION

The present invention comprises a birth control method for a female mammal which comprises administering to the mammal an amount of vitamin D compound sufficient to prevent a pregnancy from occurring or if during pregnancy to cause an abortion in the mammal. Preferably, the vitamin D compound is administered in an amount of from about 0.1 mg/kg to about 20 mg/kg per day depending upon the vitamin D compound administered. Also, the vitamin D compound is preferably administered daily to the mammal for about 3 days to about 1 month.

As used herein the term "vitamin D compound" encompasses compounds which have the C-ring, D-ring and 3β-hydroxycyclohexane A-ring of vitamin D interconnected by the 5, 7 diene double bond system of vitamin D together with a progesterone, aldehyde or alcohol side chain attached to the D-ring. In other words, the vitamin D compounds encompassed herein include those having a "vitamin D nucleus" comprising substituted or unsubstituted A-, C-, and D-rings interconnected by a 5, 7 diene double bond system typical of vitamin D together with a progesterone side chain (—COCH₃), aldehyde side chain (—COH) or alcohol side chain (—OH) attached to the D-ring.

Structurally, the vitamin D compounds encompassed may be represented by the formula

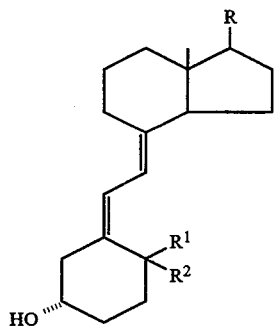

where $R^1$ and $R^2$ each represent hydrogen, or taken together $R^1$ and $R^2$ represent a methylene group and the side chain group R in the above-shown structure, represents a progesterone side chain, i.e. —COCH₃, a 22-aldehyde side chain i.e. —CHCH₃CHO, a 22-alcohol side chain i.e. —CHCH₃CH₂OH, or an alkyl side chain i.e. —CH(CH₃)₂.

Some specific examples of such compounds include vitamin D metabolites or analogues such as 20-oxo-pregnacalciferol (compound 3), and 19-nor-20-oxo-pregnacalciferol. Others include 22-oxo-homopregnacalciferol (compound 12) and 22-hydroxy-homopregnacalciferol (compound 13).

As used in the description and claims, "alkyl" represents a straight-chain or branched hydrocarbon radical of 1 to 10 carbons in all its isomeric forms, such as methyl, ethyl, propyl, isopropyl, butyl, isobutyl, pentyl, etc., and the terms "hydroxyalkyl," "fluoroalkyl" and "arylalkyl" refer to such an alkyl radical substituted by one or more hydroxy, fluoro or aryl groups respectively. An "acyl" group is an alkanoyl group of 1 to 6 carbons in all its isomeric forms, or an aroyl group, such as benzoyl, or halo-, nitro- or alkyl-substituted benzoyl groups, or an alkoxycarbonyl group of the type alkyl-O—CO—, such as methoxycarbonyl, ethoxycarbonyl, propyloxycarbonyl, etc., or a dicarboxylic acyl group such as oxalyl, malonyl, succinoyl, glutaroyl, or adipoyl. The term "aryl" signifies a phenyl-, or an alkyl-, nitro- or halo-substituted phenyl group. The term alkoxy signifies the group alkyl-O—.

This invention is more specifically described by the following illustrative examples. In these examples specific products identified by Arabic numerals (e.g. 1, 2, 3, etc.) refer to the specific structures so identified in the preceding description and in the Scheme.

EXAMPLE 1

Synthesis

Preparation of 20-oxo-pregnacalciferol 3, 1α-hydroxy-pregnacalciferol 6 and 19-nor-1α-hydroxy-pregnacalciferol 9 is accomplished via known procedures. It should be noted, however, that vitamin D contains a conjugated polyene system making it sensitive to oxygen and light. Consequently, oxygenation procedures are not used in connection with synthesis in this area. In the steroid field V. Van Rheenen: Tet. Lett. (1969) 985–988, successfully oxygenated branched aldehydes to ketones, in the presence of cupric acetate, complexed with 2,2'-bipyridyl or 1,10-phenanthroline as catalyst, the base 1,4-diazabicyclo(2.2.2)octane (DABCO) and DMF as solvent.

The above three 20-oxo-pregna-calciferols were synthesized from the corresponding and readily available vitamin D 22-aldehyde, A. Kutner et al, Tet. Lett. (1987) 28, 6129–6132, 1α-hydroxyvitamin D 22 aldehyde, A. Kutner et al, Tet. Lett. (1987) .28, 6129–6132, (calciferol 22-aldehydes) and 19-nor-1α-hydroxyvitamin D 22 aldehyde, K. L. Perlman et al, Tet. Letter., (1992) 33, 2937–2940, (1, 4, 7), by this unexpected oxygenation procedure, despite the oxygen sensitive polyene system.

3-t-Butyldimethylsilyloxy-calciferol 22-aldehydes 1, 4, and their 19-nor analog 7 were dissolved in DMF, protected from light, and air was bubbled through the solution (1 h at 40° C., RT 22 hrs, CuAc₂-2,2'-bipyridyl complex, DABCO) to give in 60–65% yield the desired 3-t.butyldimethylsilyloxy-20-oxo analogues 8 (with recovery of unconverted aldehyde). Deprotection with tetrahydrofuran-acetic acid-water (3:1:1) (40° C. for 3 hrs, RT for 22 hrs) gave in 65–70% yield the 20-oxo-pregnacalciferols 3, 6, and the 19-nor analog 9.

Analytical Data:

3. UV (in EtOH) λ max: 264 nm, λ min: 228 nm ¹H NMR (CDCl₃, 500 MHz) δ0.51 (3H, s, 18-CH₃) 2.13 (3H,s, 21-CH₃), 4.20 (1H, m, 3α-H) 4.45 (1H, m, 1β-H) 4.98 (br s, 19-E), 5.33 (1H, br s, 19 Z), 6.04 (1H, d, J=11.3 Hz, 7-H), 6.36 (1H,d, J=11.3 Hz, 6-H), Mass spectrum m/e (relative intensity) 330 (M⁺, 31) 312 (21) 183 (95) 134 (100).

6. UV (in EtOH) λ max: 264 nm, λ min: 228 nm ¹H NMR (CDCl₃, 500 MHz) δ0.51 (3H, s, 18-CH₃) 2.13 (3H,s, 21-CH₃), 3.95 (1H, m, 3α-H) 4.81 (br s, 19-E), 5.06 (1H, br s,19 Z), 6.06 (1H, d, J=11.2 Hz, 7-H), 6.22 (1H,d, J=11.2 Hz, 6-H), Mass spectrum m/e (relative intensity) 314 (M⁺, 23) 296 (2,4), 281 (15), 271 (1.5), 253 (4.6), 136 (33), 118 (73), 43 (100).

9. UV (in EtOH) λ max 243, 251.5, 261 nm ₁H NMR (CDCl₃, 500 MHz) δ0.51 (3H, s, 18-CH₃) 2.14 (3H, s, 21-CH₃) 4.06 (1H, m, 3α-H) 4.13 (1H, m, 1β-H) 5.88 (1H, d, J=11.3 Hz, 7-H) 6.29 (1H, d, J=11.3 Hz, 6-H) Mass spectrum m/e (relative intensity) 318 (M⁺, 85), 300 (5), 282 (2), 275 (35), 239 (41), 133 (100), 95 (100).

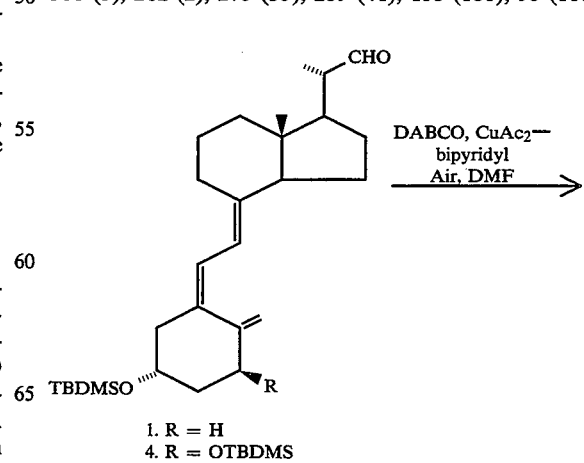

1. R = H
4. R = OTBDMS

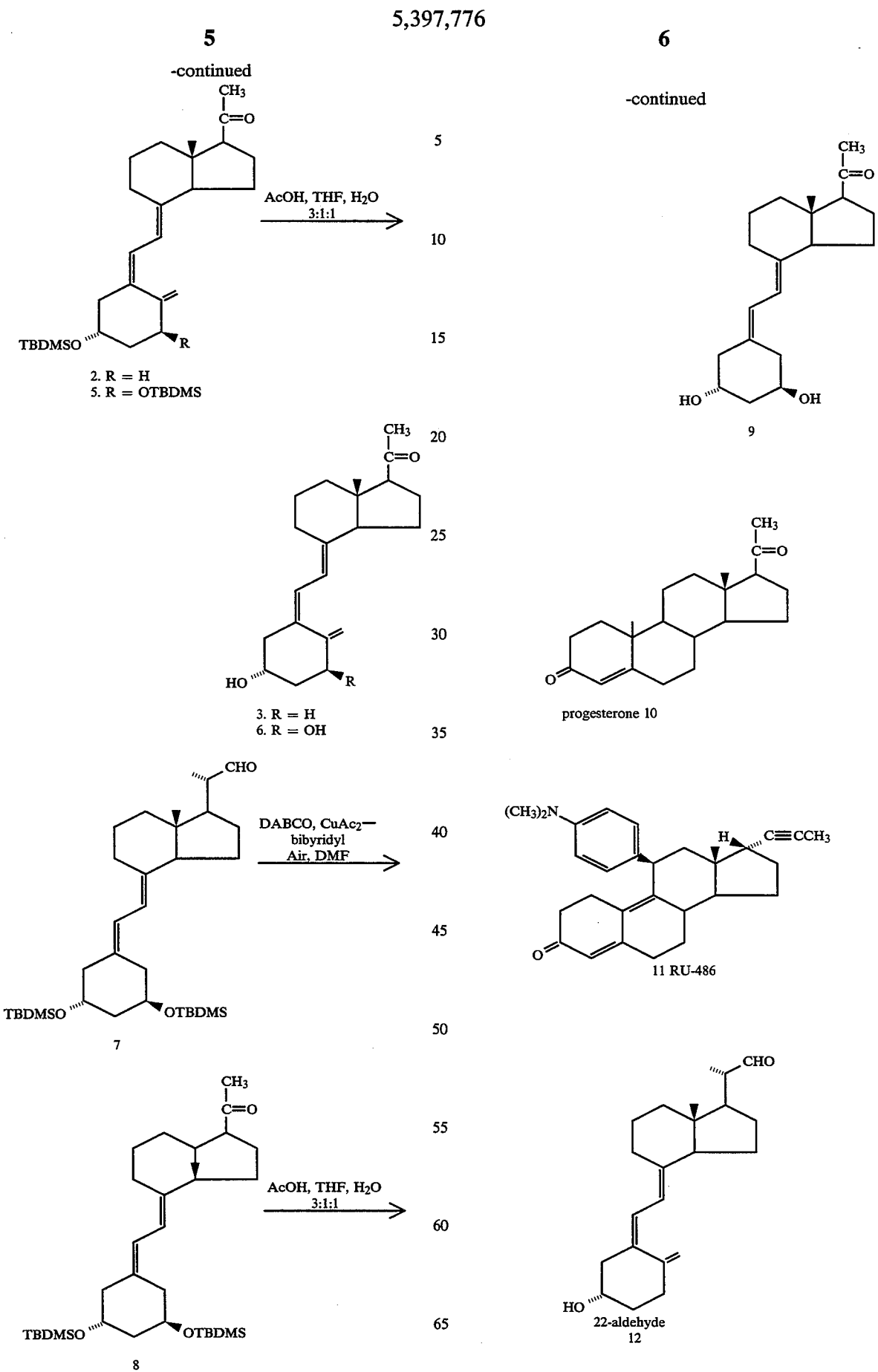

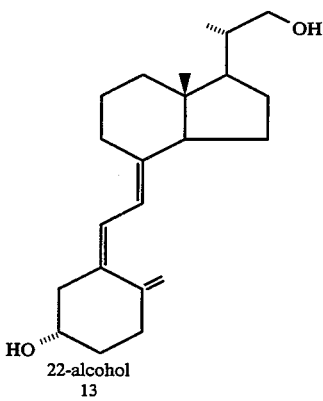

22-alcohol
13

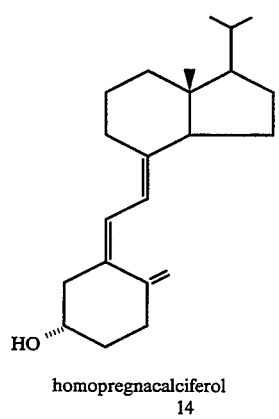

homopregnacalciferol
14

EXAMPLE 2

Receptor Binding Assay of Vitamin D Analogues with the Progesterone Receptor

This investigation was carried out to test if vitamin D analogues which share some basic structural features with progesterone can bind to the progesterone receptor to identify potential progesterone antagonists and/or agonists with vitamin D structural backbone.

Experimental Outline:

Cell culture and extract preparation: Human Breast Adenocarcinoma Cells (MCF7) extract was used as a source for progesterone receptor. The cells were grown in phenol red-free DMEM with 10% fetal calf serum (FCS) and allowed to grow to confluency. After replacing the medium with a fresh one, the cells were dosed with 10 nM Estradiol and incubated 24 hours to induce the expression of the progesterone receptor. At the end of this incubation period, the cells were washed once with Hanks Balanced Salt Solution (HBSS: 5.0 mM KCl, 0.3 mM $KH_2PO_4$ 4 138 mM NaCl, 4.0 mM $NaHCO_3$, 0.3 mM $Na_2HPO_4$, 5.6 mM D-glucose, 1.3 mM $CaCl_2$ and 0.5 mM $MgCl_2.6H_2O$). To the washed cells, Ca/Mg-free HHBSS+1 mM EDTA was added, incubated for 5 minutes at 37° C. and harvested in the same buffer. After harvesting, the cells were kept on ice afterwards. The cells were collected by centrifugation at 2000 rpm for 5 minutes at 4° C. The cells were resuspended in TDG buffer (10 mM TrisCl, pH 7.4, 0.5 mM DTT and 50% glycerol) and disrupted by sonication for 10 sec. The cell debris was removed by spinning the cell homogenate in TLA 100.2 rotor at 100,000 rpms for 10 minutes at 4° C. The supernatant was collected and stored on ice to use for the binding assay. The cell extract was always prepared fresh and used in the same day for the binding assay.

Binding Assay:

The ability of the individual vitamin D compounds to compete for binding to the progesterone receptor with the progesterone analogue, R5020, was tested by the usual hydroxyl apatite (HAP) assay. The incubation mixture was as follows:

100 μl labelled R5020 solution (20 nM)
5 μl Ethanol, or test compound at 200×
100 μl MCF7 cell extract The mixture was incubated 12-14 hours on ice. At the end of the incubation time, the samples were treated as follows:

1-To each tube, 250 μl of 50% HAP was added. After vortexing, 2 mls of TDG buffer was added for each tube.

2-The tubes were let to sit for 30 minutes at 4° C. with vortexing every 10 minutes.

3-The HAP was pelleted by spinning at 2000 rpms for 5 minutes at 4° C.

4-The pellet was washed with 2 mls/tube of TDG buffer, vortexed and pelletted like in step 3.

5-Step 4 was repeated two more times for a total of four washing steps.

6-The final pellet was extracted with 1 ml of Ethanol, vortexed and let sit at room temperature for 30 minutes with vortexing every 10 minutes.

7-The HAP was pelleted as in step 3 and 500 μl of the supernatant was counted.

Results:

The results of this screening study indicates the ability of some of the vitamin D analogues to compete with progesterone for binding to its receptor. The 20-oxo-pregnacalciferol was the most potent compound among the tested compounds in this screening study. Both the vitamin D-22-alcohol and the vitamin D-22-aldehyde analogues also competed for binding to the progesterone receptor but to a lesser extent than the 20-oxo-pregnacalciferol.

| BINDING DATA OF VITAMIN D ANALOGUES WITH THE PROGESTERONE RECEPTOR | | |
|---|---|---|
| COMPOUND | TOTAL BOUND (DPM) | % INH. |
| 1- PROGESTERONE (3H-R5020) | 2874 ± 202 | — |
| 2- + R5020 | 683 ± 93 | 76% |
| 3- + RU486 | 795 ± 171 | 73% |
| 4- + 20-OXO-PREGNACALCIFEROL | 1321 ± 190 | 53% |
| 5- + HOMOPREGNACALCIFEROL | 2557 ± 53 | 11% |
| 6- + VITAMIN D-22-ALDEHYDE | 2274 ± 146 | 21% |
| 7- + VITAMIN D-22-ALCOHOL | 1700 ± 108 | 41% |

NOTES:
1-ALL COMPETITIVE COMPOUNDS WERE PRESENT AT 200X OF THE 3H-LABELLED PROGESTERONE ANALOGUE, R5020.
2-THE SOURCE OF THE PROGESTERONE RECEPTOR WAS FROM MCF-7 CELLS INDUCED WITH ESTROGEN FOR 12 HOURS.
3-THE BINDING OF THE COMPOUNDS WITH THE RECEPTOR WAS ALLOWED TO PROCEED FOR 14 HOURS ON ICE BEFORE PROCESSING.
4-THE NUMBERS REPRESENT THE AVERAGE DPMs OF 5 SEPARATE DETERMINATIONS ± S.D.

For treatment purposes, the novel compounds of this invention can be formulated as solutions in innocuous solvents, or as emulsions, suspensions or dispersions in suitable innocuous solvents or carriers, or as pills, tablets or capsules, containing solid carriers according to conventional methods known in the art. For topical applications the compounds are advantageously formulated as creams, ointments or similar vehicles suitable for transdermal topical applications. Any such formulations may also contain other pharmaceutically-acceptable and non-toxic excipients such as stabilizers, anti-oxidants, binders, coloring agents or emulsifying or taste-modifying agents.

The compounds are advantageously administered by injection, or by intravenous infusion of suitable sterile solutions, or in the form of oral doses via the alimentary canal, or topically in the form of suitable transdermal patches. For birth control purposes, the compounds of this invention are administered to subjects in dosages sufficient to bind to the progesterone receptor (PR) so as to block the binding of progesterone to the PR thus resulting in the prevention of pregnancy or in an abortion. Suitable dosage amounts are from 0.1 to 20 mg/kg of compound per day, such dosages being adjusted, depending on the response or condition of the subject as is well-understood in the art.

Various modes of carrying out the invention are contemplated as being within the scope of the following claims, particularly pointing out and distinctly claiming the subject matter which is regarded as the invention.

We claim:

1. A birth control method for a female mammal which comprises administering to the mammal an amount of vitamin D compound sufficient to block binding of progesterone to the progesterone receptor in said mammal.

2. The method of claim 1 wherein said vitamin D compound is selected from a compound having the formula

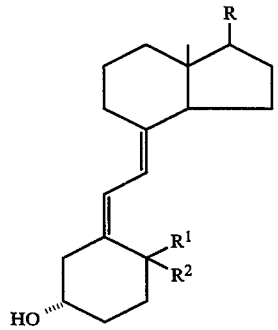

where $R^1$ and $R^2$ each represent hydrogen or taken together $R^1$ and $R^2$ represent $=CH_2$ and where R represents —COCH$_3$, —CHCH$_3$CHO, —CHCH$_3$CH$_2$OH, or —CH(CH$_3$)$_2$.

3. The method of claim 1 wherein said vitamin D compound is administered in an amount of from about 0.1 mg/kg to about 20 mg/kg per day depending upon the vitamin D compound administered.

4. The method of claim 1 wherein said vitamin D compound is administered daily to said mammal for about 3 days to about 1 month.

5. The method of claim 1 wherein said vitamin D compound is administered orally in a liquid vehicle ingestible by and non-toxic to said mammal.

6. The method of claim 1 wherein said vitamin D compound is combined with a non-toxic pharmaceutically acceptable carrier prior to administration.

7. The method of claim 1 wherein said vitamin D compound used is 20-oxo-pregnacalciferol.

8. The method of claim 1 wherein said vitamin D compound used is 1α-hydroxy-20-oxo-pregnacalciferol.

9. The method of claim 1 wherein said vitamin D compound used is 19-nor-1α-hydroxy-20-oxo-pregnacalciferol.

10. The method of claim 1 wherein said vitamin D compound used is 22-oxo-homopregnacalciferol.

11. The method of claim 1 wherein said vitamin D compound used is 22-hydroxy-homopregnacalciferol.

12. The method of claim 1 wherein said vitamin D compound is administered to women prior to the onset of a pregnancy.

13. The method of claim 1 wherein said vitamin D compound is administered to women subsequent to the onset of a pregnancy.

14. The method of claim 1 wherein the vitamin D compound is administered in a slow release formulation.

15. The method of claim 1 wherein the vitamin D compound is administered daily in divided dosages.

* * * * *

UNITED STATES PATENT AND TRADEMARK OFFICE
CERTIFICATE OF CORRECTION

PATENT NO. : 5,397,776
DATED : March 14, 1995
INVENTOR(S) : Hector F. DeLuca et al It is certified that error appears in the above-indentified patent and that said Letters Patent is hereby corrected as shown below:

Please add the following paragraph to Column 1 of the specification after the title but before the first paragraph:

---This invention was made with United States Government support awarded by the National Institutes of Health (NIH), Grant #DK-14881. The United States Government has certain rights in this invention.---

Signed and Sealed this

Twenty-third Day of January, 1996

Attest:

BRUCE LEHMAN

*Attesting Officer*　　*Commissioner of Patents and Trademarks*